United States Patent [19]

Koenig et al.

[11] 4,235,814

[45] Nov. 25, 1980

[54] MANUFACTURE OF α-HALOALKYLCARBAMYL HALIDES

[75] Inventors: Karl-Heinz Koenig, Frankenthal; Christian Reitel, Heidelberg; Dietrich Mangold, Neckargemuend, all of Fed. Rep. of Germany

[73] Assignee: BASF Aktiengesellschaft, Fed. Rep. of Germany

[21] Appl. No.: 921,312

[22] Filed: Jul. 3, 1978

[30] Foreign Application Priority Data

Sep. 17, 1977 [DE] Fed. Rep. of Germany ....... 2741980

[51] Int. Cl.$^3$ ........................................... C07C 125/03
[52] U.S. Cl. ................................................. 260/544 C
[58] Field of Search ................................... 260/544 C

[56] References Cited
FOREIGN PATENT DOCUMENTS 763948  7/1967  Canada ................................ 260/544 C

OTHER PUBLICATIONS

Angewandte Chemie, vol. 74 pp. 848–855 (1962).
Ullmanns Encylopädie der technischen Chemie, vol. 14 p. 261 (1956).
Bull. Soc. Chem. (Belg), vol. 65 pp. 291–296 (1956).

*Primary Examiner*—Paul J. Killos
*Attorney, Agent, or Firm*—Keil & Witherspoon

[57] ABSTRACT

α-haloalkylcarbamyl halides are manufactured by reacting N-tert.-alkyl-N-1-alkenyl-carbamyl halides with a hydrogen halide at from −78° C. to +80° C.

The α-haloalkylcarbamyl halides, e.g. α-chloroalkylcarbamyl chlorides, especially α-chloroethylcarbamyl chloride, prepared by the process of the invention, are valuable starting materials for the manufacture of surface-coating raw materials, textile coatings, dyes, drugs and crop protection agents.

7 Claims, No Drawings

MANUFACTURE OF α-HALOALKYLCARBAMYL HALIDES

The present invention relates to a process for the manufacture of α-haloalkylcarbamyl halides by reacting N-tert.-alkyl-N-alkenyl-carbamyl halides with a hydrogen halide at from −78° C. to +80° C.

Angewandte Chemie, 74 (1962), 848–855 discloses the reaction of alkylcarbamyl chlorides with elementary chlorine to give the corresponding α-chloroalkylcarbamyl chlorides. However, the products which result are mixtures, both in respect of the degree of halogenation and in respect of the position of the halogen atoms entering the molecule. The process is unsatisfactory in respect of yield and purity of the end product, and does not permit simple and economical operation.

We have found, surprisingly, that α-haloalkylcarbamyl halides are obtained in a simple and original manner if N-tert.-alkyl-N-(1-alkenyl)-carbamyl halides are reacted with a hydrogen halide at from −78° C. to +80° C.

Further, we have found the novel α-haloalkylcarbamyl halides of the formula

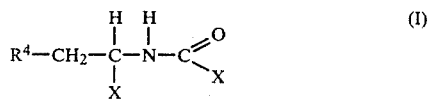

where $R^4$ is alkyl of 1 to 20 carbon atoms and X is halogen.

Compared to the conventional process, the process of the invention gives α-haloalkylcarbamyl halides more simply and more economically, and in better yield and in greater purity. Working up is substantially simpler since the reaction mixture obtained does not contain a large number of different components. All these advantageous results are surprising, since the formation of a variety of reaction products was to be expected from the great reactivity of the starting materials. It was also to be expected that α,β-unsaturated nitrogen compounds would polymerize or hydrolyze very easily under the influence of acids. For example, N-vinylpyrrolidone is converted to a mixture of oligomers under the influence of even small amounts of an inorganic acid (Ullmanns Encyclopädie der technischen Chemie, volume 14, page 261). Bull. Soc. Chim. Belg., 65 (1956), 291–296 discloses that vinyl isocyanate is hydrolyzed by aqueous 12-normal hydrochloric acid in acetone to give acetaldehyde.

Employing the process of the invention, a quantitative fragmentation into a tert.-alkyl halide and an α-haloalkylcarbamyl halide takes place, in accordance with the equation below:

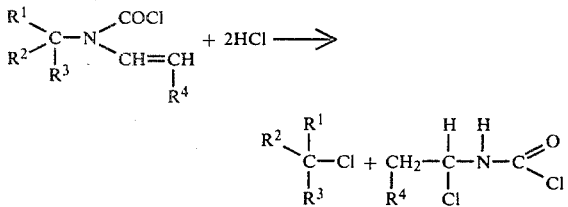

Suitable tertiary alkyl radicals, where $R^1$, $R^2$ and $R^3$ may be identical or different, are those of 4 to 20 carbon atoms, and especially of 4 to 12 carbon atoms. Specific examples are tert.-butyl and tert.-amyl. Accordingly, the radicals $R^1$ to $R^3$ in the formula given may be alkyl of 1 to 6 carbon atoms, especially methyl and ethyl.

$R^4$ is advantageously hydrogen or alkyl of 1 to 20, especially 1 to 12, preferably 1 to 6, carbon atoms; preferred meanings are hydrogen, methyl and ethyl.

The reaction of a tert.-alkyl-N-(1-alkenyl)-carbamyl halide with a hydrogen halide makes it possible to prepare the heat-labile halide, especially α-chloroalkylcarbamoyl chloride, in a particularly pure form and under mild reaction conditions, whilst the reaction of elementary halogen with an alkylcarbamyl halide (Angewandte Chemie, loc. cit.) gives product mixtures in respect of the position of the halogen atom entering the molecule, and in respect of the degree of halogenation. The tert.-alkyl halide also formed in the reaction is inert under the conventional reaction conditions and need therefore as a rule not be removed for carrying out the further reactions of the α-chloroalkylcarbamyl halide.

The addition reaction of a hydrogen halide with a N-tert.alkyl-N-(1-alkenyl)-carbamyl halide may be carried out in the presence or absence of a solvent. Advantageously, however, the starting material is dissolved in an inert solvent or mixture of solvents.

Suitable solvents which are inert under the reaction conditions are hydrocarbons, e.g. pentane, hexane, cyclohexane, octane and methylcyclohexane; halohydrocarbons, e.g. methylene chloride, chloroform, carbon tetrachloride, 1,2-dichloroethane, 1,2-dichloropropane and propyl bromide; aromatic hydrocarbons, e.g. benzene, toluene, chlorobenzene and o-dichlorobenzene; aromatic ethers; aliphatic ethers, e.g. diethyl ether, diisopropyl ether, tetrahydrofuran and dioxane; ketones, e.g. acetone, ethyl methyl ketone and acetophenone; and esters, e.g. ethyl formate, ethyl acetate, propionic acid esters and higher-boiling esters.

Because of the reactivity of the resulting α-haloalkylcarbamyl halides, the reaction is preferably carried out under anhydrous conditions, but in principle it can also be carried out with aqueous hydrochloric acid.

The concentration of the solutions of the N-tert.-alkyl-N-(1-alkenyl)-carbamyl halides may be varied within wide limits, a concentration range of from 1 to 50 percent by weight being used preferentially.

The addition reaction with a hydrogen halide is carried out at from +80° C. to −78° C., advantageously at from −78° C. to +40° C., preferably at from −10° C. to +20° C., under atmospheric or superatmospheric pressure, continuously or batchwise. The hydrogen halide, advantageously hydrogen bromide and especially hydrogen chloride, is used in the stoichiometric amount or in excess, preferably in an amount of from 2 to 2.2 moles per mole of carbamyl halide.

The reaction may specifically be carried out as follows: the N-tert.-alkyl-N-(1-alkenyl)-carbamyl halide is introduced into an inert solvent and hydrogen chloride gas is introduced at, for example, from −10° C. to 0° C. After completion of the reaction, the reaction solution is stirred for some time longer, for example for 15 minutes, and excess hydrogen halide is blown out by means of $N_2$.

The α-haloalkylcarbamyl halides, e.g. α-chloroalkylcarbamyl chlorides, especially α-chloroethylcarbamyl chloride, prepared by the process of the invention, are valuable starting materials for the manufacture of surface-coating raw materials, textile coatings, dyes, drugs and crop protection agents.

In the Examples, parts are by weight.

EXAMPLE 1

161.5 parts of N-tert.-butyl-N-vinylcarbamoyl chloride at 0° C. are introduced into the reaction vessel and 75 parts of hydrogen chloride gas are passed in over 60 minutes. The reaction mixture is then stirred for a further 15 minutes at the same temperature, and excess HCl is blown out with $N_2$. Tert.-butyl chloride is stripped off under reduced pressure and the α-chloroethylcarbamoyl chloride is recrystallized from $CCl_4$. 136 parts (95% of theory) are obtained; melting point 20/21° C.

EXAMPLE 2

175.5 parts of N-tert.-amyl-N-vinylcarbamyl chloride are introduced into the reactor at 10° C. and 75 parts of HCl are passed in whilst stirring.

After completion of the reaction, the reaction mixture is stirred for a further 30 minutes at room temperature and excess HCl is blown out with $N_2$.

The tert.amyl chloride is stripped off under reduced pressure.

130 parts (91.5% of theory) of α-chloroethylcarbamyl chloride of melting point 20° C. remain.

We claim:

1. A process for the manufacture of an α-haloalkyl-carbamyl halide, wherein a N-tert.-alkyl-N-(1-alkenyl)-carbamyl halide is reacted with a hydrogen halide at from −78° C. to +80° C.
2. A process as claimed in claim 1, where the reaction is carried out at from −78° C. to +40° C.
3. A process as claimed in claim 1, wherein the reaction is carried out at from −10° C. to +20° C.
4. A process as claimed in claim 1, wherein the reaction is carried out in the presence of a solvent which is inert under the reaction conditions.
5. The process of claim 1 wherein the hydrogen halide is reacted with a compound of the formula

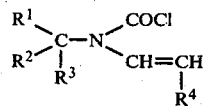

wherein $R^1$, $R^2$ and $R^3$ are identical or different alkyl radicals of 1 to 6 carbon atoms and wherein $R^4$ is hydrogen or alkyl of 1 to 20 carbon atoms.

6. The process of claim 5 wherein $R^1$, $R^2$ and $R^3$ are methyl or ethyl.
7. The process of claim 6 wherein $R^4$ is hydrogen, methyl or ethyl.

* * * * *